United States Patent [19]
Prostkoff

[11] Patent Number: 5,549,678
[45] Date of Patent: Aug. 27, 1996

[54] CRANIAL PROSTHESIS

[76] Inventor: Melvin E. Prostkoff, 9 Garrison La., Madbury, N.H. 03820

[21] Appl. No.: 393,212

[22] Filed: Feb. 23, 1995

Related U.S. Application Data

[63] Continuation of Ser. No. 44,980, Apr. 8, 1993, abandoned, which is a continuation of Ser. No. 782,599, Oct. 25, 1991, Pat. No. 5,218,975.

[51] Int. Cl.$^6$ .............................. A61F 2/28; A61F 5/00; A61F 13/00
[52] U.S. Cl. ................. 623/16; 602/14; 602/17; 602/72
[58] Field of Search ................ 623/11, 15; 606/69, 606/70, 71; 128/846, 857; 602/17, 14, 72, 12; 2/411, 412

[56] References Cited

U.S. PATENT DOCUMENTS

| | | | |
|---|---|---|---|
| 4,600,618 | 7/1986 | Raychok, Jr. et al. | 428/92 |
| 4,796,611 | 1/1989 | Wardlaw | 128/87 R |

Primary Examiner—Debra S. Brittingham
Attorney, Agent, or Firm—Wolf, Greenfield & Sacks, P.C.

[57] ABSTRACT

An external cranial protective device which provides a protective and aesthetically pleasing function in protecting the brain of an individual where a section of the bone has been removed from the skull or face.

7 Claims, 2 Drawing Sheets

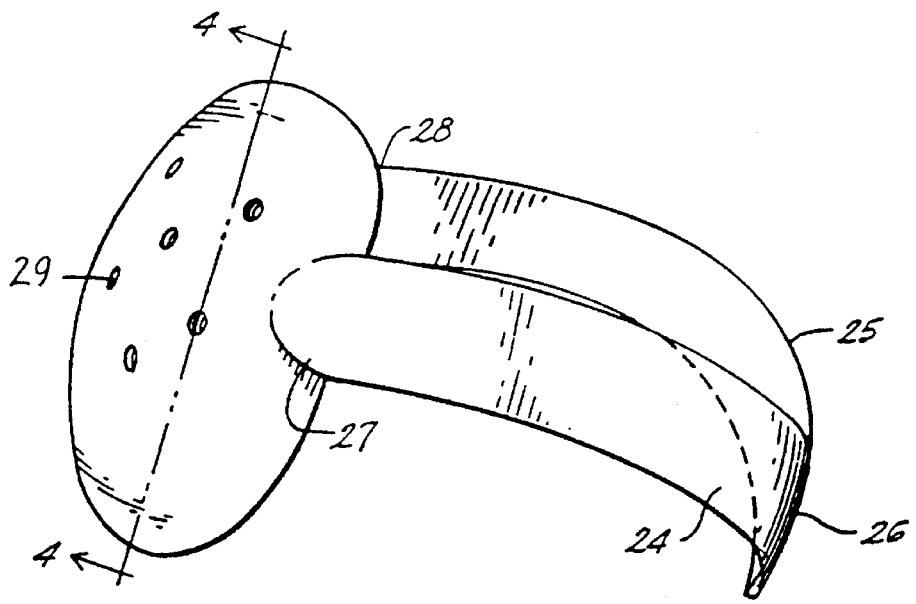
FIG. 3
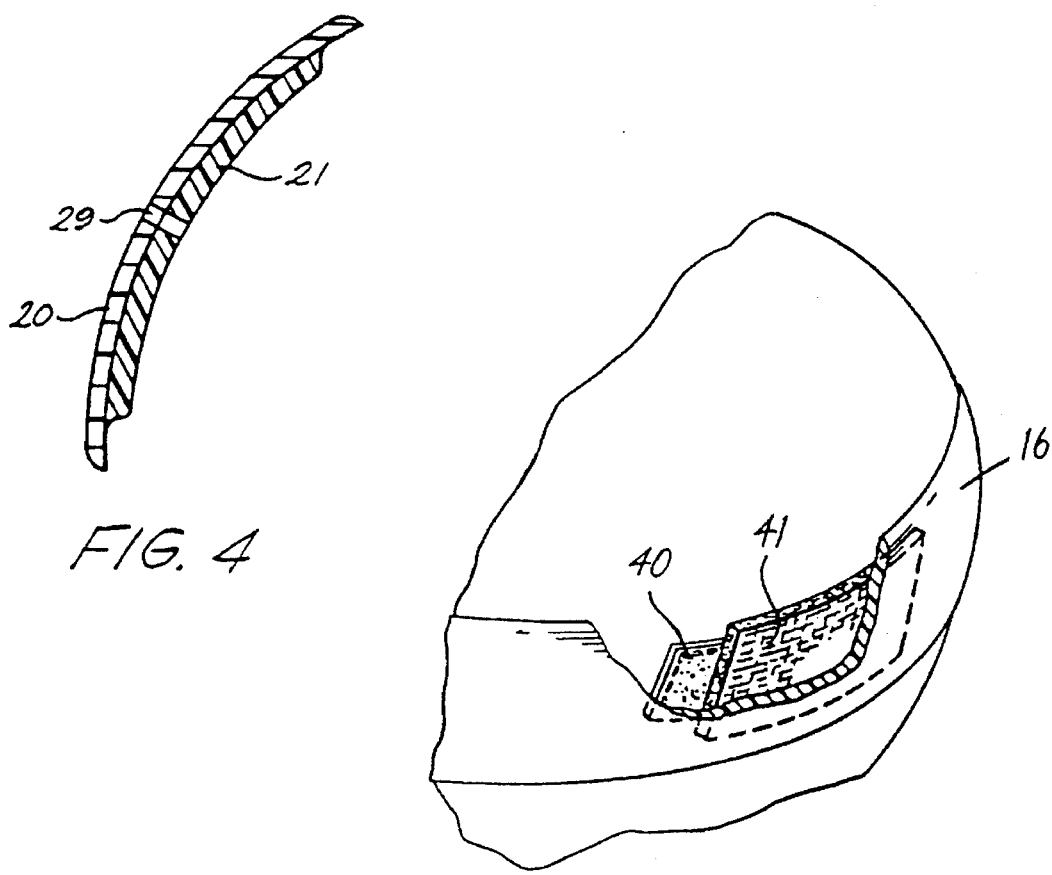
FIG. 4
FIG. 5

CRANIAL PROSTHESIS

RELATED APPLICATIONS

This application is a continuation of U.S. application Ser. No. 08/044,980 filed Apr. 8, 1993 which is a continuation of U.S. application Ser. No. 07/782,599 filed Oct. 25, 1991 now U.S. Pat. No. 5,218,975 filed Jun. 15, 1993.

BACKGROUND OF THE INVENTION

There are many medical conditions wherein part of the cranial bone is removed or is genetically absent so as to leave a depression in the skull with the brain underlying the skin of the depression and substantially exposed to the environment. Conditions of this type include instances where surgery on traumatic depressed skull fractures, hematomas, brain and/or skull abscess and other neurosurgical procedures of various kinds result in removal of bone to enable access to the brain underlying the skull, and it is not medically feasible at that time to replace the removed skull bone parts.

Often, after cranial surgery, after a period of time, a support plate is fitted over or into the cranial bone to, in effect, act as a replacement for the bone. This brings the contour of the skull back to substantially its original shape for aesthetic purposes and also protects the underlying brain. However, it is often necessary to wait one year or more before such plates can be inserted under the skin after the original surgery or bone removal.

The prior art often resorts to the use of football helmets or other helmets to protect the skull and hide the cosmetic defect and deformity prior to insertion of the plate. Where there is a delay between cranial bone removal and plate placement, the brain often remains vulnerable to trauma from external sources in a depression in the skull and does not expand until such time as the plate is put into position, due to the effects of atmospheric pressure.

It has now been found that an external cranial prosthesis can be used to protect the brain and provide cosmetic repair to the skull of an individual disfigured by bone removal or defect in a rapid and uncomplicated procedure.

FIELD OF THE INVENTION

The field of this invention is the protection and cosmetic improvement of the skull of an individual after bone removal or genetic defect, to protect the brain of an individual and provide cosmetic advantage.

SUMMARY OF THE INVENTION

It is an object of this invention to provide a cranial device for protecting the brain of an individual, which device can be light weight, structurally strong and cosmetically pleasing.

Another object of this invention is to provide a method of protecting the brain of the individual by using a device in accordance with preceding objects.

Still another object of this invention is to provide a cranial device in accordance with the preceding objects, which can be cosmetically enhanced as by paint, makeup, skin tone, hair and the like.

Still another object of this invention is to provide a device and method in accordance with the preceding objects, wherein the device can be individually customized and used in conjunction with various attachment means for providing simple and preferably removable attachment to the skull or scalp of an individual.

According to the invention, a method of protecting the brain of an individual, who has a section of bone removed from the skull or face, is provided. The method uses an aesthetically pleasing external prosthetic open to view. The method comprises forming a plastic sheet material, preferably in place over the skull by hand-shaping the sheet to the overall contour of the skull. The prosthetic is positioned about a depression in the skull caused by bone removal. The depression is covered by the skin or scalp and is bounded by an underlying peripheral edge of skull bone which supports the prosthetic and has a portion of the brain unprotected by bone at the base of the depression.

The sheet material is hardened in the contour of the skull with a peripheral edge of the sheet material overlying the skin or scalp over the skull bone peripheral edge by at least one-eighth of an inch and spaced from the brain by a chamber corresponding to the volume that is normally filled by bone and by body components prior to bone removal. The sheet material has a shock resistant value sufficient to protect the brain from shock and damage by forces directed to the head, while presenting an aesthetically pleasing outer surface to view. Means are provided for holding the prosthetic in place without shifting when subject to external trauma.

It should be understood that reference to the skull and cranial bone is meant herein to include all head bones of the individual.

Preferably, the sheet material is shaped on a side of the skull corresponding to the removed bone section, as near as possible consistent with bone remaining on the skull and then finally shaped over the depression itself.

The preferred prosthetic comprises a formed base sheet having a peripheral edge designed and dimensioned to overly a peripheral edge of cranial bone about a cranial depression. The sheet is formed to a hardened form to provide shock protection at normal atmospheric conditions.

A mounting means for the sheet is provided and can be in the form of an extension of the sheet material encircling the head of the user. In the preferred form, the prosthetic is toned to be aesthetically pleasing or aesthetically pleasing coverings, artificial hair or other cosmetic enhancements are provided to give an overall aesthetically pleasing appearance to the protective prosthetic in use.

It is a feature of this invention that prosthetics of this type can be made quickly, efficiently and can easily be customized to an individual. The materials can be materials known in making prosthesis for the body and, thus, can be easily handled and formed by a wide variety of medical personnel on a routine basis, using standard methodology. The prosthetics are relatively inexpensive to make, highly versatile to cover depressions of various sizes and shapes, lightweight, easy to use without disruption of lifestyle and highly protective. Ventilation can be provided with ease, as can various cosmetic enhancements and various attachment means to the skull or scalp of an individual.

BRIEF DESCRIPTION OF THE DRAWINGS

The above and other objects, advantages and features of the present invention will be better understood from a reading of the following specification, in conjunction with the enclosed drawings, in which:

FIG. 3 is a side view of an embodiment thereof not positioned on the skull of the user;

FIG. 4 is a cross-sectional view thereof taken through line 4—4 of FIG. 3; and

FIG. 5 is a detail of an alternate embodiment thereof.

DESCRIPTION OF PREFERRED EMBODIMENTS

Figure 1:
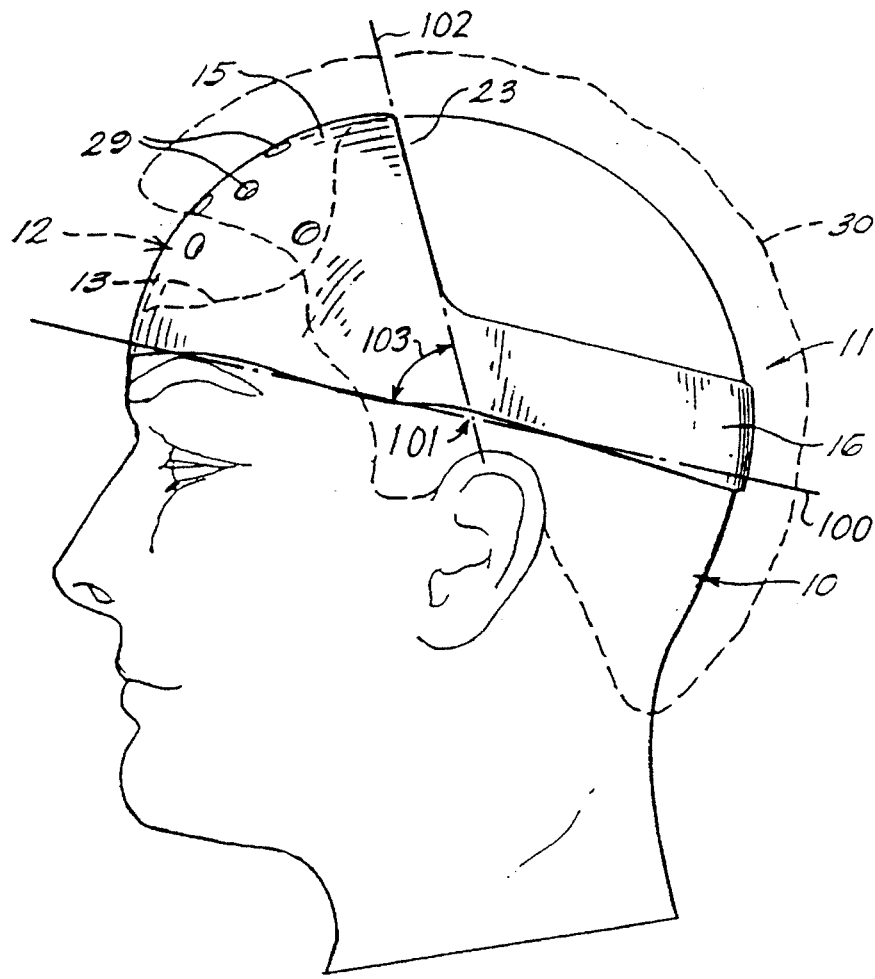
FIG. 1 is a side view of a cranial prosthetic in accordance with the present invention shown mounted on the head of a user.
Figure 2:
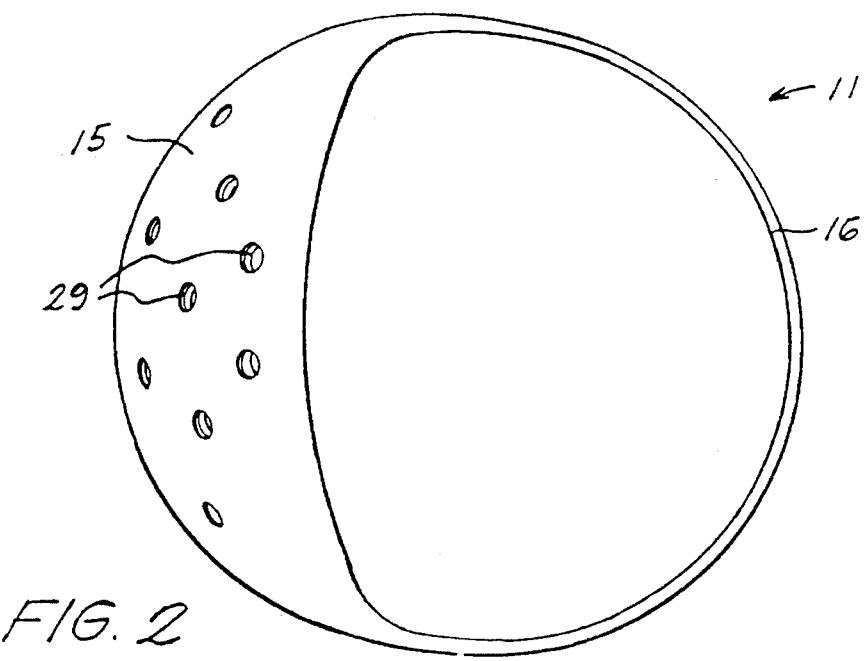
FIG. 2 is a top plan view thereof.

With reference now to the drawings and more particularly FIG. 1, the head of an individual is shown at 10 wearing the prosthetic 11 of this invention over a depression 12 present in the skull.

The depression in the skull or cranial bone can be caused by congenital absence of bone or bone removal by surgical procedures, as in traumatic depressed skull fractures, as well as in the removal of bone to reach the brain to correct abscess conditions, hematomas, tumor conditions, infections and the like.

Typically, the depression 12 is formed by removal of the bone while the skin or scalp 13 of the individual overlies the depression with the brain tissue underlying the skin or scalp 13 in the depression 12. The brain, not shown, is considered to be any neural or other tissue underlying the skin or scalp at the base of the depression.

The prosthesis itself has a base plate 15 to which is attached a strip 16 of plastic material. The plastic is preferably any thermo formable plastic such as thermoplastic polycaprolactone having good shock resistance when in place over the depression on the cranial bone and which can be easily formed. CaraForm, a trademark product of Lohmann Products of Tulsa, Okla., is a useful sheet material for forming the prosthesis 11 of this invention.

The base plate or sheet protective member 15 is formed into curved shape from a flat sheet thermoplastic material such as CaraForm of a polycaprolactone. The polycaprolactone can be supported or on a net substrate so that it will not run or stretch when softened. Other synthetic organic polymeric materials such as thermoplastics can also be used in place of polycaprolactone. Suitable thermoplastics include urethanes, polypropylene and the like. Preferably, such thermoplastics soften well above normal environmental temperatures, but below temperatures that are too hot to easily and conveniently handle and shape. Softening temperatures above 120° F. are preferred.

CaraForm, in a preformed sheet having a thickness of for example, 1.2 milimeters, provides sufficient shock resistance for most situations and has desirable softening and hardening properties.

In some cases, as in the preferred embodiments shown in FIGS. 1–4, the base plate 15 is formed of a first thermoplastic sheet 20 and a second thermoplastic sheet 21 overlying and bonded thereto, both of CaraForm material. The peripheral edge 23 of the base plate 15 overlies the cranial bone aperture in the skull by at least one-eighth inch (⅛"), preferably entirely around the periphery of the depression, to form an overlap sufficient to provide strength against shock to the plate in ordinary environmental use of the prosthesis 11. The base plate and the entire prosthetic covers substantially less than the entire skull area and preferably less than one half the skull area. Thus, bumping one's head at normal or expected amounts would not cause damage to the underlying skull.

The curved base thermoplastic sheet 15 defines a sector of less than 90°, which means that, as set forth above, the base plate covers substantially less than the entire skull area and preferably less than one-half the skull area. This can be seen in FIG. 1 where a line through the bottom of the base plate 15 and band 16 shown at 100 when intersected by a radius through the center of such line at 101 with the second radius being denoted at 102, defines an, angle 103 of less than 90°.

The base plate 15, whether it be of a single plastic sheet or multiple plastic sheets, or some other laminated construction, is designed to provide protection to the brain. Thus, an ultimate tensile strength at −15° to 45° C. should be greater than 1000 psi as measured according to standard test method ASTM E8. The strength in bending, under the same temperature range, when measured by standard test method ASTM D2344, shall be greater than 6.8 psi. Preferably, stiffness values are such that at 20° +3° C., the elastic modulus in tension is greater than 37,500 psi, as measured according to standard test method ASTM E8. The elastic modulus in bending for 20° +3° C. shall be greater than 13,000 psi, as measured according to standard test method ASTM D747.

Preferably, the plate can be formed from a single or plural layers of thermosetting or thermoplastic materials. Thermosetting materials can be rigid or elastomeric. When setting or curing materials are used, rather than thermal shaping, the setting reaction is preferably triggered chemically or by radiation. Heating can be carried out by infrared radiation or radio frequency electromagnetic energy, including dielectric heating and induction heating, to obtain a softened sheet to allow shaping. Preferably, thermoplastic polymers are used which have required strength and rigidity over the range of normal temperatures encountered by the individuals using the plates.

The base plates are such as not to crack, craze or otherwise show evidence of material failure at the expected conditions of use which include temperatures of from −20° to 105° F. They are preferably resistant to common household chemicals and common disinfecting chemicals, including most soaps and shampoos. With the CaraForm material of the present invention, when a cranial prosthesis is formed as in FIG. 1, impact resistance is substantial. Using a hockey player's eye and face protective equipment test ASTM F513-81 (1984), cracking and crazing is shown to be avoided in normal use conditions. Thus, when carrying out that test with a sphere of material in accordance with FIG. 1, and having this sphere with a diameter of 7.22+0.1 inches and a chord diameter of 6.00+0.05 inches in either single thickness or double thickness layers, at a test temperature of −15° C. to about 45° C., cracking and crazing was avoided after the sample was equilibrated at test temperature and a steel material weighing 1.24 pounds was dropped through a guide tube of 1.5 inch PVC DWV ASTM D2665, with the sample centered under the guide tube on a steel plate, using both direct vision and a magnifier, no cracking, crazing or other type of material failure was found.

The preferred embodiment has a band 16 formed by two strips of CaraForm 24, 25 formed in place about the contour of the head of the user to hold the base plate 15 in place properly over the aperture without deforming the bone of the skull. Any means for holding the base in place could be used in place of the CaraForm bands. In the preferred embodiment, the bands are joined at 26 to each other and at 27 and 28 by bonding or thermal fusion to the base plate 15. Note that the base plate 15 follows the contour of the cranial bone, leaving a depression on the underside of the base corresponding to the original bone and neural brain tissue, scalp and the like that filled the depressed area prior to bone removal.

It will be easily understood that the prosthesis 11 can be formed of any lightweight, strong, cosmetically pleasing material. Paint, makeup, skintoner and the like can be used to provide desirable cosmetic effects. Similarly, hair, wigs and artificial hair coloring can be used to, again, enhance cosmetic effect of the prosthetic.

The means for attaching the base plate 15 to the skull can vary greatly. Although a thermoplastic integral band formed of strips 24 and 25 is preferably used, an elastic band, velcro strips, or the like can be attached to the base plate and positioned in place on the skull.

In one embodiment, illustrated at FIG. 5, hooks or loops of a velcro attachment means 40 can be sewn to the scalp and the hooks or loops corresponding to those sewn to the scalp can be used on a fabric band 41 or totally velcro band attached to the plate 15 and affixed in place for removable attachment to the velcro sewn to the scalp.

In some cases, the velcro attachment can be made directly to the base plate 15 and the band 16 eliminated. In some cases, a wig such as 30 can be worn entirely over the prosthesis of this invention and the remainder of the scalp, to totally hide the prosthesis while the prosthesis supports the wig to give the normal contour of the skull. In some cases, part of the prosthetic extends below the line of the wig and is aesthetically enhanced. A wig can be attached to the prosthetic by velcro if desired.

In a preferred method of protecting the brain of an individual who has a section of bone removed, CaraForm, a polycaprolactone is used to form the plate 15. Preferably, the scalp is covered with the plastic CaraForm plastic sheet which has first been heated in hot water to a temperature of about 165° F. to soften it. A piece of plastic wrap like Saran Wrap is placed over the scalp to protect the patient from thermal injury from the heated CaraForm. The rough shape of the skull can be obtained by forming the sheet on the side of the head not having the depression or on a corresponding portion of the head having a contour nearest to that which would conform to the removed bone. The somewhat soft sheet material is then applied over the hole to finally shape it by hand after it is hardened slightly. The so-formed sheet, having the contour of the skull, is then preferably marked and cut to at least a one-eighth inch overlap and preferably as much as one centimeter overlap around the periphery of the depression. If hardened first, the base 15 can be reheated to soften and allow cutting to shape with a scissor.

In a next step, the base plate 15 can be sanded, cosmetically modified, textured, painted or have artificial hair or other cosmetic attachments attached. Holes can be drilled in the plate, as shown at 29, to ventilate the depression.

When CaraForm is used, the plate will remain in shape and provide sufficient shock protection to normal shocks encountered by the body in use. The patient is preferably cautioned not to heat the plate 15 above 120° F., although it will not fully soften until it reaches its forming temperature. The strips 24 and 25 can be cut of CaraForm heated to 165° F. to the shape of the head and then bonded by epoxy or thermal fusion to the plate 15.

The thermoplastic sheet material of the base plate 15 (whether a single layer or plural layers), preferably, is thin, having a preferred thickness of from 0.020 inch to 0.25 inch; lightweight having an overall weight of preferably less than one pound. The material is protective against ordinary shock to which the body is exposed, such as bumping into objects, being unintentionally hit by objects and the like.

In the embodiment of FIG. 4, an additional sheet material 21 is heated and shaped to conform to the prior shaped sheet 20 and then bonded thereto by epoxy or thermal fusion to provide a dual-layered protective and cosmetic device for use in covering cranial depressions in accordance with this invention. The plate 15 can be a single thickness or can be plural layered.

It will be understood that although a specific embodiment has been shown and described, the prosthetic can have a base shaped to any reasonable size aperture in a cranial bone. For example, apertures in the frontal, temporal, parietal or occipital portions of the skull can be treated in accordance with this invention.

The prosthesis 11 is supported about the peripheral edge of the depression on the skin of the user and can be removed as desired for washing and the like.

By the use of this device, a cosmetically acceptable injury protective device can be provided by the use of substantially conventional forming procedures and methods.

What is claimed is:

1. A skull shaped prosthetic device for protecting a brain within a skin covered skull bone of an individual, said individual having a jaw, the skull having a normal original shape and contour, the skull having a section of bone absent from the skull bone above a portion of said brain resulting in forming a depression in an area of said skin overlying said brain portion and covering the skull, and defining a peripheral edge, while providing an aesthetically pleasing prosthetic for the individual, said prosthetic device comprising a curved base thermoplastic sheet formed to said contour of the skull substantially in said original shape of the skull before absence of said bone and covering and overlapping said depression and covering less than one-half of the skull the curved base defining a sector of less than 90° said base defining a sheet peripheral edge and an attachment means extending from the sheet peripheral edge to encircle the opposite side of the skull above the ear, said sheet having a substantial width and being dimensioned to protect substantially only said area covering said portion of said brain and having said sheet peripheral edge extending over said underlying peripheral edge of said depression in the skull by at least one-eighth inch and supported by the skull to provide shock resistance, said attachment means supported by said skull and having a width substantially less than the width of said sheet material for holding said thermoplastic sheet on the skull of the user, said attachment means for holding said thermoplastic sheet on the skull of a user being on said skull and not extending below the jaw of the individual.

2. A prosthetic device in accordance with claim 1, wherein said plastic sheet acts as a protective and supportive plate and has a layer bound thereto to provide additional shock resistance and support.

3. A prosthetic device in accordance with the prosthetic device of claim 1, wherein said attachment means is an encircling thermoplastic band joined to said plate.

4. A prosthetic device in accordance with the prosthetic device of claim 1 wherein said attachment means for holding comprises a detachable means for allowing application and removal of said base plastic sheet to the skull and scalp and said sheet is provided with ventilation holes.

5. A prosthetic device for protecting a brain within a skin covered skull bone of an individual, said individual having a jaw and chin, the skull having a normal shape and contour and having a section of bone absent from the skull bone above a portion of the brain resulting in forming a depression in an area of the skin overlying and covering said brain portion of the skull and defining a peripheral edge, while providing an aesthetically pleasing prosthetic for the individual, said prosthetic device comprising a generally concave shaped skull plate, said prosthetic device comprising a curved base formed of a thermoplastic sheet material which is formed to the contour of the skull, substantially in the original shape of the skull before absence of said bone, said sheet material having a substantial width and being dimensioned to protect substantially only said area covering said portion of the brain and having a sheet peripheral edge extending over said underlying peripheral edge of said depression in the skull by at least 1/8", but short of providing a helmet covering and covering less than one half of the skull area, and supported by the skull to provide shock resistance, the curved base defining a sector of less than 90°, said sheet peripheral edge having an attachment means extending from the sheet peripheral edge to encircle the opposite side of the skull above the ear, said attachment means supported by said skull and having a width substantially less than the width of said sheet material above the chin of a user for holding said plastic sheet on the skull and scalp of the user, said base being resistant to cracking and crazing and having an ultimate tensile strength from −15° to 45° C. above 1000 psi ASTM EB, a strength in bending from −15° C. to 45° C. above 6.8 psi ASTM D2344, an elastic modulus in tension at 20°+3° C. of greater than 37,500 ASTM E8, and an elastic modulus in bending greater than 13,000 psi ASTM D747 at 20°+3° C.

6. A prosthetic device in accordance with claim 5 wherein an encircling continuous band is interconnected with said plate and fused thereto to act as said means for holding.

7. A prosthetic device in accordance with claim 5, and further including velcro attachment means for attaching said plate to the scalp of a user.

\* \* \* \* \*